US007097626B2

(12) United States Patent
Louis et al.

(10) Patent No.: US 7,097,626 B2
(45) Date of Patent: Aug. 29, 2006

(54) MASSAGE TOOL FOR USE IN APPLYING A COLD TREATMENT

(76) Inventors: John Louis, 269 Latrobe Ave., Northfield, IL (US) 60093; Herm Schneider, 1529 Tulane Dr., Naperville, IL (US) 60565

( * ) Notice: Subject to any disclaimer, the term of this patent is extended or adjusted under 35 U.S.C. 154(b) by 402 days.

(21) Appl. No.: 10/454,377

(22) Filed: Jun. 4, 2003

(65) Prior Publication Data

US 2004/0249323 A1 Dec. 9, 2004

(51) Int. Cl.
*A61H 7/00* (2006.01)
*A61F 7/02* (2006.01)

(52) U.S. Cl. ......................... 601/15; 601/135; 601/138

(58) Field of Classification Search .................. 601/15, 601/17, 72, 73, 80, 135, 137, 138; 607/104, 607/112, 114; 426/421, 134, 515; 215/227; 38/74, 92; 62/356

See application file for complete search history.

(56) References Cited

U.S. PATENT DOCUMENTS

| | | | | |
|---|---|---|---|---|
| 1,593,858 | A * | 7/1926 | Venable | 294/5.5 |
| 2,946,207 | A * | 7/1960 | Hulterstrum | 249/92 |
| 3,411,463 | A * | 11/1968 | Moseres | 249/92 |
| 4,688,339 | A * | 8/1987 | Tsai | 38/77.7 |
| 6,250,593 | B1 * | 6/2001 | Palu | 248/117.2 |

* cited by examiner

*Primary Examiner*—Danton Demille
*Assistant Examiner*—Manuj Agarwal
(74) *Attorney, Agent, or Firm*—John C. Shepard

(57) ABSTRACT

A massage tool for use in performing an ice massage including an anchor extending from the bottom of a base for extending into a mold for receiving a block of ice. The massage tool includes a handle by which the tool can be manipulated, which provides thermal isolation from the ice attached to the tool. The tool is weighted to reduce the amount of additional force needed to apply the desired pressure during the massage, thereby reducing hand and muscle fatigue of the therapist providing the massage.

14 Claims, 3 Drawing Sheets

MASSAGE TOOL FOR USE IN APPLYING A COLD TREATMENT

FIELD OF THE INVENTION

The invention pertains to a massage tool, and more specifically, a massage tool which receives a contact substance that has been changed from a liquid physical state to a solid physical state, such as water to ice, for use in applying a cold treatment.

BACKGROUND OF THE INVENTION

Therapists apply various techniques when treating an individual, dependant upon the condition of the individual. Some techniques can require persistant application, which can be quite taxing on a therapist, especially therapists who provide treatment generally unassisted.

Some therapists have made use of various tools designed to more effectively and/or more easily apply certain techniques. Different tools have had varying degrees of success. Some tools may improve some aspects related to applying a particular therapy, while sometimes making other aspects worse. Other tools may fall short of the desired effect, or may be the victim of ever increasing demands that they were never intended to meet and/or address. Consequently, there is an ever increasing demand to develop more effective techniques, some of which may only be possible with an appropriate tool. Furthermore, there is a demand to increase the effectiveness of existing tools.

Several techniques require the targeted application of pressure and/or force. At least a couple of examples include muscle stripping, trigger point, friction, and effleurage. Furthermore, the addition of force to other types of therapies can sometimes improve their effectiveness. However, the persistent application of force can, in some instances, be taxing on a therapist. Consequently, techniques and/or tools, which can assist in the application of force or can more effectively apply an existing force can serve to relieve some of the strain on a therapist applying a particular technique.

Furthermore, tools which help combine the effective application of force with other therapies may also be beneficial. For example, ice treatments have historically been used to stop bleeding and correspondingly reduce swelling, thereby correspondingly limiting the further trauma to an area. More recently, ice massages have been used to more effectively apply a chill to an area, and enable the temperature effects to penetrate deeper and more quickly. It is believed that applying a force during an ice massage further enhances the penetration of the chilling effects.

Still further, techniques or tools that help to eliminate other impediments to the application of an effective treatment, either to the recipient of the treatment, or the person applying the treatment, would additionally be beneficial.

SUMMARY OF THE INVENTION

A massage tool is provided including a base having a top and a bottom, and an anchor coupled to the bottom of the base. The anchor is adapted to extend from the bottom of the base into a contact substance in liquid form, and is further adapted to be captivated by the contact substance as the contact substance undergoes a physical state change between a liquid and a solid. The massage tool further includes a handle having a first end and a length, wherein the handle is coupled to the base of the massage tool proximate the first end of the handle, and wherein the length of the handle has at least a first portion which extends away from the base.

In at least one embodiment of the invention, the massage tool is weighted to enhance the mass of the tool.

In at least a further embodiment of the invention, the contact substance is contained in a mold, which is adapted to receive the massage tool, where the anchor of the massage tool extends into the contact substance when the massage tool is received by the mold and the mold is filled with contact substance in liquid form.

In yet a still further embodiment of the invention, the massage tool has a temperature insulative outer surface.

A further aspect of the present invention provides for a mold adapted for receiving a liquid contact substance and a massage tool having a base, which when the contact substance is solidified, the contact substance is attached to the massage tool and can be released from the mold. The mold has a cup including one or more side surfaces and a bottom surface for receiving a liquid contact substance, wherein the side surfaces have a top edge, which follows the shape of the base of the massage tool.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

Figure 1:
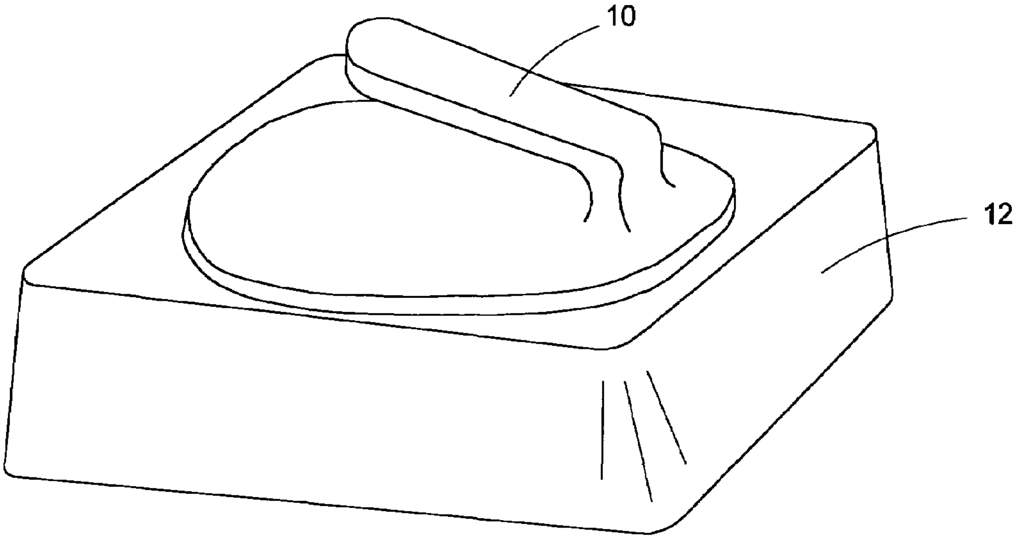
FIG. 1 is a perspective view of a massage tool and a mold for forming a solid contact substance, which is attached to the base of the massage tool for use in applying a temperature altering treatment, in accordance with at least one embodiment of the present invention.

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

Figure 2:
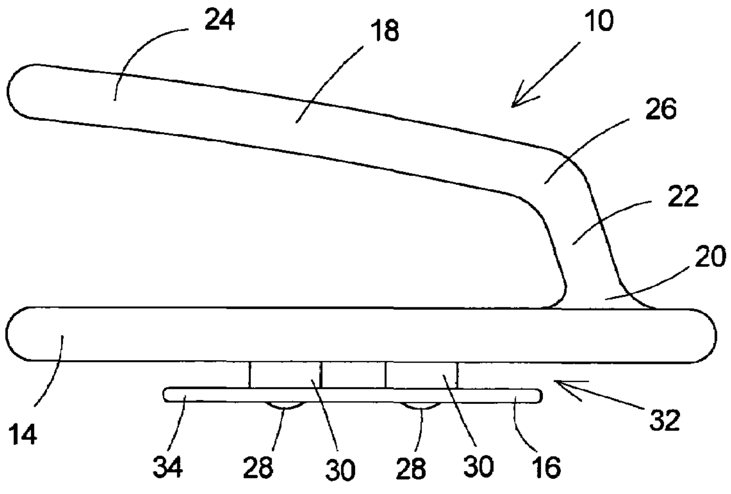
FIG. 2 is a side view of the massage tool, illustrated in FIG. 1.
Figure 3:
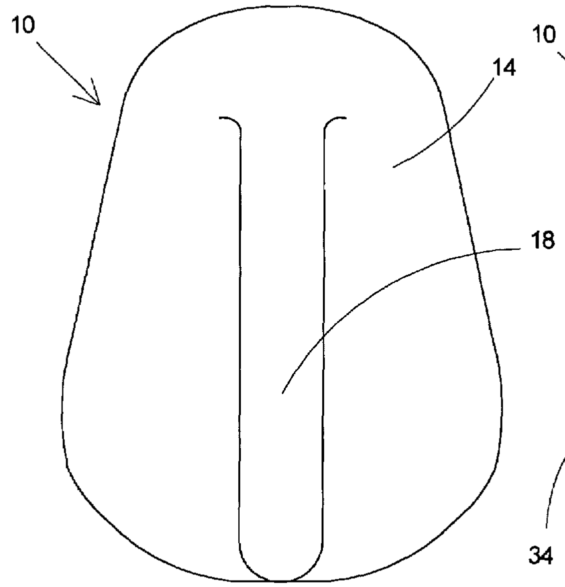
FIG. 3 is a top view of the massage tool, illustrated in FIGS. 1 and 2.
Figure 4:
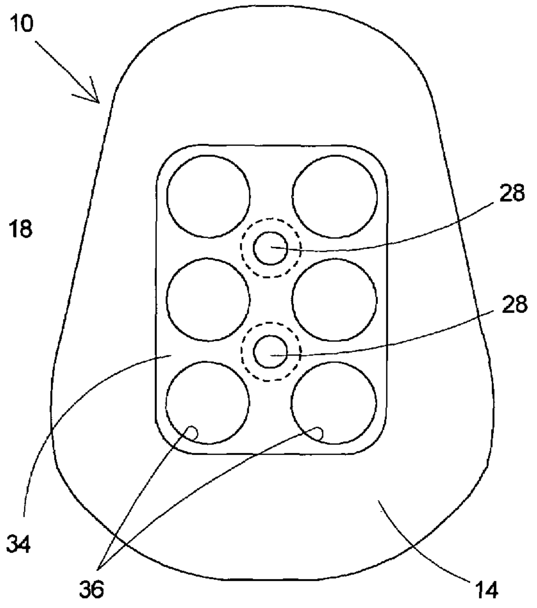
FIG. 4 is a bottom view of the massage tool, illustrated in FIGS. 1–3.

Referring now to the drawings in greater detail, there is illustrated in FIG. 1 a perspective view of a massage tool 10 and a mold 12 for forming a solid contact substance, which is attached to the base of the massage tool for use in applying a temperature treatment, in accordance with at least one embodiment of the present invention. As can be seen in FIGS. 2–4, the massage tool includes a base 14, an anchor 16 coupled to the bottom of the base 14, and a handle 18 coupled to the top of the base 14.

The anchor 16 is adapted to extend from the bottom of the base 14 into a contact substance, which is in liquid form, and which is located in the mold 12. The temperature located around the mold 12 is then lowered below a threshold temperature where the contact substance will transition between a liquid physical state and a solid physical state. As the contact substance changes into a solid physical form, the anchor 16 which was immersed into the contact substance, while in liquid form, is captivated within the contact substance. The contact substance can then be removed from the mold 12 while attached to the anchor 16 of the massage tool 10. The contact substance, while attached to the massage tool 10 can be used to apply a cold treatment to a recipient of therapy.

In at least the illustrated embodiment, the handle 18 is coupled to the base at a first end 20 of the handle 18, where the handle includes a first portion 22 that extends away from the base 14, and a second portion 24 that extends from the first portion 22 in a direction that follows along the top surface of the base 14, where the junction between the first portion 22 and the second portion 24 forms an elbow 26. In at least one embodiment the first portion 22 of the handle 18 is coupled to the base a predetermined distance away from the front edge of the base, which in at least the illustrated embodiment has been found to improve the overall balance of the tool 10.

As configured and arranged in the illustrated embodiment, the handle 18 presents at least a couple of options for manipulating the tool 10 via one's hand. A first option enables a user to press the palm of their hand on the top surface of the second portion 24 of the handle 18, while curling one or more of their fingers around the second portion 24 of the handle 18. This allows the user's thumb to rest against the front surface of the first portion 22 of the handle 18, and the index finger to push against the back surface of the first portion 22 of the handle 18. A second option enables the user to press the palm of the their hand against the elbow 26 joining the first portion 22 of the handle 18 to the second portion 24 of the handle 18, wherein the user's fingers extend back along the top surface of the second portion 24 of the handle 18 and the user's thumb wraps around the back side of the first portion 22 of the handle 18. In this way the massage tool can be manipulated.

One of the benefits of providing for multiple hand positions relative to the manipulation of the tool is to distribute between multiple hand locations the point of repeated impact relative to the tool during the manipulation thereof. This can enable portions of the user's hand to have some recovery time, while other hand manipulation positions are being used, thereby slowing the onset of or reducing hand fatigue.

Additionally, in at least the illustrated embodiment, the hand tool is weighted thereby limiting the amount of force necessary to be applied by the hand to produce the desired pressure relative to the recipient of the therapy, which can further reduce hand strain. In at least one embodiment, the weight of the massage tool, in combination with the contact substance initially weighs three pounds. As a result, a supplemental force is only necessary, when three pounds is insufficient for creating the desired amount of pressure. While the illustrated embodiment has a weight of approximately three pounds, the desired weight can be tailored to more readily accommodate the weight to the user's specific needs, as well as accommodate other forms of therapies. For example, weights as low as twelve ounces, and as high as six pounds, in related applications have been found to be useful.

In the present embodiment, the tool includes iron as a base material, to which a large percentage of the tool's weight can be attributed. However, one skilled in the art will readily recognize, that the tool could be made from other materials without departing from the teachings of the present invention. The tool is then covered by a non-thermally conductive layer, such as a synthetic rubber sold under the trademark Neoprene by DuPont. The layer of synthetic rubber provides a good surface for the user to grip, as well as a degree of isolation from the temperatures associated with the cold block of material attached to the anchor 16 of the massage tool 10. The synthetic rubber additionally provides an amount of resistance to corrosion for the underlying materials, which as noted above in the discussion associated with the illustrated embodiment, includes at least a fair amount of iron.

The anchor 16 is coupled to the base via one or more fasteners 28. It the illustrated embodiment, the anchor 16 is coupled to the base by a pair of fasteners 28, each located at a corresponding one of a pair of connection points laterally displaced apart along the bottom surface of the base 14. One or more spacers 30 are used with each fastener 28 to establish and maintain a gap 32 between the base 14 and the anchor 16 through which the contact substance will flow around and captivate the anchor 16. After the fasteners 28 are applied, the anchor 16 and the fasteners 28 are spot welded to make the connection more secure.

The anchor 16 additionally includes one or more wings, which extend laterally along the base away from the fasteners. In the illustrated embodiment, the one or more wings 34 include one or more circular voids 36. One of the advantages of using circular voids 36 is the avoidance of any sharp corners, that might precipitate cracking of the contact substance. Similar to the gap between the base and the anchor formed via the presence of spacer, the voids similarly allow the contact substance to more readily encapsulate the anchor by providing fluid paths through which the contact substance can flow while in liquid form. While the illustrated embodiment uses circular shaped void, other void shapes could be used, while still benefitting from the teachings of the present invention.

Figure 5:
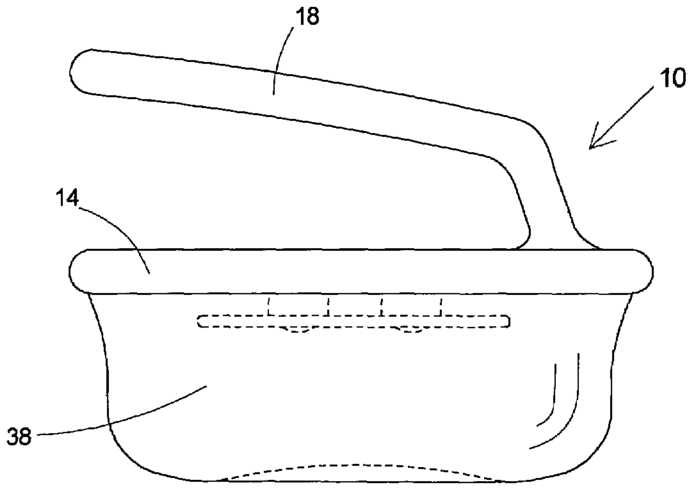
FIG. 5 is a side view of a massage tool with an attached contact substance in solid form.

In the illustrated embodiment, the contact substance is or contains water, which turns into or contains ice when in solid form 38. FIG. 5 illustrates a side view of a massage tool 10 with an attached block of ice 38. The block of ice has a shape that is consistent with the contour of the cup surface in the mold 12. The contour of the cup surface can be more readily seen in FIGS. 6 and 7.

Figure 6:
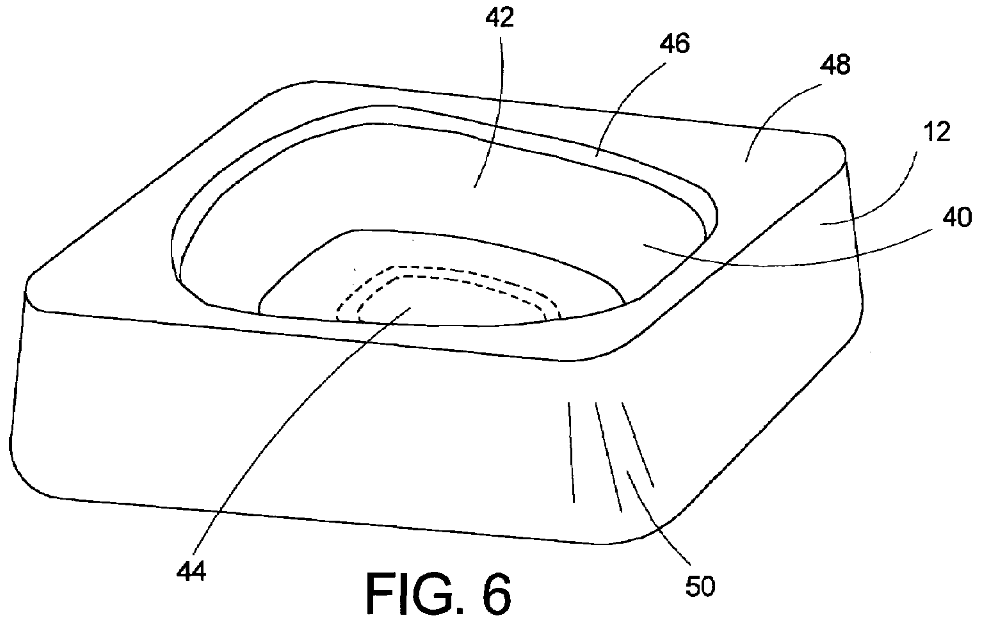
FIG. 6 is a perspective view of the mold adapted for forming a contact substance in solid form, which is attached to the base of the massage tool, illustrated in FIG. 1.

FIG. 6 illustrates a perspective view of the mold adapted for forming a contact substance in solid form, such as ice, which is attached to the base of the massage tool, as illustrated in FIG. 5. The mold 12 includes a cup 40, which is adapted for receiving water or a contact substance, while in liquid form. The cup 40 includes one or more side surfaces 42 and a bottom surface 44. The bottom surface 44 is arched upward toward the center of the bottom surface 44, so as to avoid downward deflection when the ice or contact substance freezes and possibly expands. The arched bottom surface further provides for a block of ice whose form when removed from the mold has an arched bottom surface that more readily can be used to massage a curved surface, like the soft tissue around a protruding bone. The side surfaces 42 have a top edge 46, which follows the shape of the base 14 of the massage tool 10, that is recessed a slight distance from the outer edge of the base 14.

Figure 7:
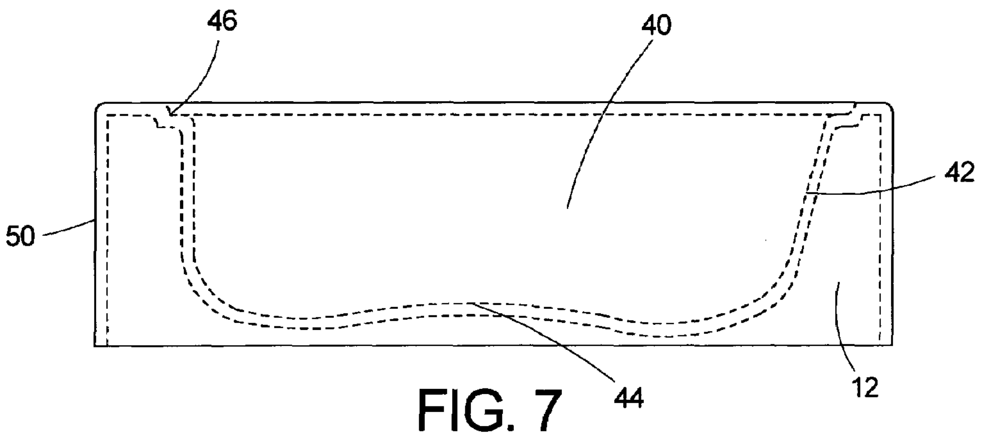
FIG. 7 is a side view of the mold, illustrated in FIG. 6, with hidden lines shown.

The mold 12 additionally includes a top surface 48 in the form of a lip, which extends outward from the top edge of the side surfaces of the cup 40. The mold 12 still further includes a skirt 50, which extends downward from the outer edge 46 of the top surface 48 and extends around the sides of the mold 12. In at least one embodiment, the mold 12 is formed via a vacuum molding process, wherein the side walls of the mold 12 are sufficiently thick to resist deflection resulting from any forces created by any expansion or contraction of the ice (water)/contact substance during any physical state changes. However, the walls are sufficiently thin to enable the mold to be flexed by the user, thereby more readily enabling the release of the frozen block of ice/contact substance. FIG. 7 illustrates a side view of the mold, illustrated in FIG. 6, with hidden lines shown, which highlights the thickness of the mold walls, in accordance with at least one embodiment.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A massage tool manipulable by a user to apply cold therapy by manually positioning an attached frozen contact substance in physical contact with a therapy recipient, said massage tool comprising:

a generally planar base having opposed top and bottom surfaces connecting along an outer peripheral edge;

a handle having at least one portion fixed to the base and an elongate user grip portion overlying said base top surface and extending generally parallel therealong in spaced relation;

an anchor having opposed top and bottom surfaces connecting along an outer peripheral edge, said anchor underlying said base bottom surface with said anchor top surface opposed to and extending generally parallel therealong in spaced relation; and, at least one connector extending between and fixed to said base and anchor to hold said anchor in spaced, suspended relation below said base such that said anchor is substantially isolated from said base, said anchor being submersible in the contact substance when in a liquid state to substantially encapsulate said anchor when in a solid state such that the contact substance may be carried by said anchor below said base when frozen.

2. The massage tool of claim 1 wherein said anchor has at least one opening extending between its top and bottom surfaces, whereby the contact substance in a liquid state may flow through the opening and in a solid state extend through the opening.

3. The massage tool of claim 1 wherein said connectors are fixed to the top surface of said anchor inwardly spaced from said anchor peripheral edge.

4. The massage tool of claim 1 wherein said base peripheral edge spans an area greater than that spanned by said anchor peripheral edge and lies radially outward thereof.

5. The massage tool of claim 1 wherein said handle user grip portion is disposed generally over and spaced from the center of said base top surface permitting a portion of a user's hand to be placed between the handle and the base center when gripping said handle.

6. The massage tool of claim 1 wherein the weight of the tool is at least ¾ of a pound.

7. The massage tool of claim 6 wherein the weight of the tool does not exceed 6 pounds.

8. The massage tool of claim 1 wherein the tool has an encapsulating outer surface of insulative material.

9. The massage tool of claim 1 wherein the tool has an interior formed of metal and an encapsulating outer layer of insulative material.

10. The massage tool of claim 1 further including a separate mold adapted to hold the contact substance in a liquid state while it is being frozen to said anchor, said mold comprising a cup defined by side and bottom walls and defining a cavity and an opening at an upper end opposite said cup bottom wall, a lip having an inner edge adjacent said cup opening and extending laterally outward therefrom to an outer edge, and a skirt around said cup extending downward from said lip outer edge to a bottom, said mold cup side wall forming a recess around said cup opening below the level of said lip corresponding to the base peripheral edge such that said base may be cooperatively located therein, and said cavity being sized relative to said anchor such that the massage tool may be positioned in said recess with said base over said cup opening and said anchor within said cavity spaced from said mold cup side and bottom walls and submerged in the liquid contact substance contained in said cavity such that the contact substance may be frozen to substantially encapsulate said anchor therewithin.

11. The massage tool of claim 10 wherein said mold is formed from plastic.

12. The massage tool of claim 10 wherein said mold cup bottom wall is upwardly convex, whereby the contact substance when frozen in said mold cup will have a concave bottom.

13. The massage tool of claim 10 wherein said mold cup side and bottom walls and their respective junctions are curved, whereby the corners and edges of the contact substance when frozen in said mold cup will be rounded.

14. A means for enabling a user to apply cold massage therapy by manually positioning a frozen contact substance in physical contact with a therapy recipient, said enabling means comprising a massage tool and a mold, said massage tool including a base having opposed top and bottom surfaces connecting along an outer peripheral edge, a handle having at least one portion fixed to the base and an elongate user grip portion overlying said base top surface and extending therealong in spaced relation, a relatively thin anchor having opposed top and bottom surfaces connecting along an outer peripheral edge, said anchor underlying said base bottom surface with said anchor top surface opposed to and extending therealong in relatively close spaced relation, said anchor having at least one opening extending between its top and bottom surfaces, a connector extending between and fixed to said base and anchor to hold said anchor in spaced, suspended relation below said base such that said anchor is substantially isolated from said base, the tool having an encapsulating outer surface of insulative material and having a weight of at least ¾ of a pound and not exceeding 6 pounds, said mold including a cup defined by side and bottom walls and defining a cavity adapted to hold the contact substance in its liquid and solid states and an opening at an upper end opposite said cup bottom wall, a lip having an inner edge adjacent said cup opening and extending laterally outward therefrom to an outer edge, and a skirt around said cup extending downward from said lip outer edge to a bottom, said mold cup side wall forming a recess around said cup opening below the level of said lip corresponding to the base peripheral edge such that said base may be located therein, said cavity being sized relative to said anchor such that the massage tool may be cooperatively positioned in said recess with said base over said cup opening and said anchor within said cavity spaced from said mold cup side and bottom walls and submerged in the liquid contact substance contained in said cavity such that the contact substance may be frozen to substantially encapsulate said anchor therewithin, whereby the mold holds the contact substance initially in a liquid state which is thereafter frozen to a solid state, and whereby the massage tool when removed from the mold with the frozen contact substance carried by said anchor below said base is manipulable by a user to position the frozen contact substance in physical contact with a therapy recipient.

* * * * *